(12) United States Patent
Jeong et al.

(10) Patent No.: US 9,867,776 B2
(45) Date of Patent: Jan. 16, 2018

(54) TRANSDERMAL DRUG DELIVERY SYSTEM HAVING MULTI-LAMELLAR EMULSION STRUCTURE

(71) Applicant: NEOPHARM CO., LTD., Yuseong-gu, Daejeon (KR)

(72) Inventors: Se Kyoo Jeong, Daejeon (KR); Ji Yeon Park, Daejeon (KR); Min Seok Kim, Daejeon (KR); Jong Mi Lim, Daejeon (KR)

(73) Assignee: NEOPHARM CO., LTD., Daejeon (KR)

( * ) Notice: Subject to any disclaimer, the term of this patent is extended or adjusted under 35 U.S.C. 154(b) by 48 days.

(21) Appl. No.: 14/902,102

(22) PCT Filed: Jul. 1, 2014

(86) PCT No.: PCT/KR2014/005856
§ 371 (c)(1),
(2) Date: Dec. 30, 2015

(87) PCT Pub. No.: WO2015/002435
PCT Pub. Date: Jan. 8, 2015

(65) Prior Publication Data
US 2016/0367475 A1    Dec. 22, 2016

(30) Foreign Application Priority Data
Jul. 1, 2013    (KR) .................. 10-2013-0076434

(51) Int. Cl.
*A61K 47/28* (2006.01)
*A61K 9/00* (2006.01)
(Continued)

(52) U.S. Cl.
CPC ............ *A61K 9/0014* (2013.01); *A61K 9/107* (2013.01); *A61K 31/192* (2013.01);
(Continued)

(58) Field of Classification Search
CPC ...................................................... A61K 47/28
See application file for complete search history.

(56) References Cited

U.S. PATENT DOCUMENTS

| | | |
|---|---|---|
| 6,221,371 B1 | 4/2001 | Baik et al. |
| 2004/0087564 A1* | 5/2004 | Wright et al. ....... A61K 31/573 514/179 |
| 2007/0286835 A1 | 12/2007 | Park et al. |

FOREIGN PATENT DOCUMENTS

| | | |
|---|---|---|
| EP | 1236462 A1 | 9/2002 |
| KR | 10-1998-0034991 A | 8/1998 |

(Continued)

OTHER PUBLICATIONS

B.D. Park et al., "The Characterization of Molecular Organization of Multilamellar Emulsions Containing Pseudoceramide and Type III Synthetic Ceramide", J Invest Dermatol, Oct. 2003, pp. 794-801, vol. 121.

(Continued)

*Primary Examiner* — Benjamin Packard
(74) *Attorney, Agent, or Firm* — Sughrue Mion, PLLC (57) ABSTRACT

Provided is a transdermal drug delivery system, which is a delivery system for transdermal absorption, having a multi-lamellar emulsion structure, including: lipids including long-chain amides, sterols, fatty acid and fatty alcohol; an emulsifier; oil; and at least one drug for transdermal administration. The transdermal drug delivery system in a multi-lamellar emulsion structure, according to the present invention, has a lamellar structure in which a layered structure visible in stratum corneum intercellular lipids of the human body is repeated, and thus has an excellent skin barrier effect and enables a drug to be effectively partitioned through skin lipids, thereby obtaining an excellent drug delivery effect.

14 Claims, 5 Drawing Sheets

(51) Int. Cl.
    *A61K 9/107* (2006.01)
    *A61K 31/573* (2006.01)
    *A61K 31/192* (2006.01)
    *A61K 31/196* (2006.01)
    *A61K 31/405* (2006.01)
    *A61K 31/5415* (2006.01)
    *A61K 31/542* (2006.01)
    *A61K 47/10* (2017.01)
    *A61K 47/12* (2006.01)
    *A61K 47/18* (2017.01)

(52) U.S. Cl.
    CPC .......... *A61K 31/196* (2013.01); *A61K 31/405* (2013.01); *A61K 31/542* (2013.01); *A61K 31/5415* (2013.01); *A61K 31/573* (2013.01); *A61K 47/10* (2013.01); *A61K 47/12* (2013.01); *A61K 47/18* (2013.01); *A61K 47/28* (2013.01)

(56) References Cited

FOREIGN PATENT DOCUMENTS

| KR | 10-2000-0055082 A | 9/2000 |
|---|---|---|
| KR | 10-2002-0070154 A | 9/2002 |
| KR | 10-2006-0089903 A | 8/2006 |
| KR | 10-2007-0117800 A | 12/2007 |
| KR | 10-2012-0041294 A | 5/2012 |
| WO | 02/067900 A1 | 9/2002 |
| WO | 2007/112712 A1 | 10/2007 |

OTHER PUBLICATIONS

International Searching Authority International Search Report for PCT/KR2014/005856 dated Oct. 10, 2014.

European Patent Office; Communication dated Jan. 20, 2017, in counterpart European Patent Application No. 14819797.3.

Hyun Jung Kim, et al. "Pseudoceramide-Containing Physiological Lipid Mixture Reduces Adverse Effects of Topical Steroids", Allergy, Asthma & Immunology Research, Apr. 2011, vol. 3, No. 2., 7 pages total.

Mueller-Goymann, C.C., et al. "Sustained release from reverse micellar solutions by phase transformations into lamellar liquid crystals", Journal of Controlled Release, 1993, vol. 23, 10 pages total.

\* cited by examiner

TRANSDERMAL DRUG DELIVERY SYSTEM HAVING MULTI-LAMELLAR EMULSION STRUCTURE

CROSS REFERENCE TO RELATED APPLICATIONS

This application is a National Stage of International Application No. PCT/KR2014/005856 filed Jul. 1, 2014, claiming priority based on Korean Patent Application No. 10-2013-0076434 filed Jul. 1, 2013, the contents of all of which are incorporated herein by reference in their entirety.

TECHNICAL FIELD

The present invention relates to a transdermal drug delivery system using a composition capable of improving the partitioning of an active ingredient into the stratum corneum.

BACKGROUND ART

The epidermis of the skin is composed of stratum corneum, stratum lucidum, stratum granulosum, stratum spinosum, and stratum basale. Among them, the stratum corneum is one of the most important portions in the body, which exists in an outermost layer of the skin and serves to prevent water loss and serves as a primary defense against harmful contaminants in an external environment.

The stratum corneum is largely composed of keratinocytes and stratum corneum intercellular lipids. Here, the keratinocytes, which are cells differentiated and formed from the stratum basale of the epidermis, are composed of protein called keratin, and the stratum corneum intercellular lipids are filled between the keratinocytes. The stratum corneum intracellular lipids are mainly composed of ceramide, cholesterol, fatty acids, and the like. In the normal skin, the stratum corneum intracellular lipids exist in a multi-lamellar structure, and it is known that the multi-lamellar structure is a physical basis of significantly low material permeability of the skin. The low permeability as described above is an important factor of an epidermal permeability barrier function of the skin. In addition, a skin barrier function may perform roles of moisturizing the skin and physically, chemically, and microbiologically protecting the skin, and the like.

A theory about structural features of the stratum corneum and roles of constituting components depending on the structural features, particularly, roles of the stratum corneum intercellular lipids having the multi-lamellar structure has been initially suggested by Peter M. Elias (Department of Dermatology, San Francisco State University), through a "brick and mortar model" in 1970s, and thereafter, availability of this model has been proven through various follow-up researches (The Characterization of Molecular Organization of Multi-lamellar Emulsions Containing Pseudoceramide and Type III Synthetic Ceramide. J. Invest. Dermatol. 2003 October; 121(4):794-801.).

A drug delivery system is a medical technology of minimizing adverse effects of a drug and maximizing efficacy and an effect thereof to allow the required amount of the drug to be efficiently delivered. The drug is delivered through various routes such as an oral route, a parenteral route, a transdermal route, a mucosal route, a transplant route, and the like. Among them, in a case of administering the drug through the transdermal route, it may be easy to adjust an administration dose of the drug, there is no systemic effect, and bioavailability of the drug may be increased by preventing drug denaturation generated at the time of intestinal absorption.

As described above, the multi-lamellar structure of the stratum corneum intercellular lipids becomes a physical basis of significantly low permeability of the skin. However, in a transdermal drug delivery system or topical formulation, the low permeability as described above has been a large obstacle in developing effective formulations. In the development of the transdermal drug delivery system or topical formulation up to now, as a method of overcoming the problem as described above, a method of physically or chemically changing or destroying the multi-lamellar structure of the stratum corneum intracellular lipids, or the like, has been used.

In the transdermal drug delivery system, a delivery route of the drug through the stratum corneum is subjected to a series of the following processes:

1) a drug is dissolved from a vehicle, 2) the dissolved drug is partitioned into the stratum corneum, particularly, stratum corneum intercellular lipids, 3) the drug passes through the stratum corneum while being diffused through the stratum corneum intercellular lipids, 4) the drug moves to the stratum granulosum while being partitioned in a boundary portion between the stratum corneum and the stratum granulosum, and 5) the drug is diffused to the stratum granulosum, the stratum spinosum, and the stratum basale again. It may be explained from the process as described above that after dissolution of the drug from the matrix, a process of "partitioning-diffusion" is repeated. Partitioning of drug in the stratum corneum is changed depending on partition coefficient of the drug between the matrix and the stratum corneum, in more detail, between the stratum corneum intercellular lipids.

The present inventors developed a composition having a multi-lamellar structure similar to that of the stratum corneum intercellular lipids through a prior study, and it was confirmed that this composition assisted in reinforcing and repairing a skin barrier function. The present inventors found that since this composition has a structure similar to that of the stratum corneum intercellular lipids, in a case of a topical formulation using the corresponding composition as a matrix, a primary partitioning process (partitioning of drug between the matrix and the stratum corneum) of the above-mentioned transdermal drug delivery system may be effectively promoted, such that the partitioning of the drug in the stratum corneum is increased, and as a result, a content of the drug in the stratum corneum is increased, thereby completing the present invention.

DISCLOSURE

Technical Problem

An object of the present invention is to provide a drug delivery system capable of promoting the partitioning of an active ingredient into the stratum corneum, in more detail, stratum corneum intercellular lipids by using a composition having a multi-lamellar structure similar to that of the stratum corneum intercellular lipids in the human body as a matrix. Another object of the present invention is to provide an excellent transdermal drug delivery system capable of improving a content of an active ingredient in the stratum corneum and continuously delivering the active ingredient.

Technical Solution

In one general aspect, a transdermal drug delivery system, which is a delivery system for transdermal absorption, having a multi-lamellar emulsion structure, includes: lipids including long-chain amides, sterols, fatty acids and fatty alcohols; an emulsifier; oil; and at least one drug for transdermal administration.

In the present invention, the multi-lamellar emulsion structure is not limited, but may simultaneously have a periodicity phase of 9.0 to 11.0 nm and a periodicity phase of 5.2 to 7.2 nm in small angle X-ray diffraction analysis. It may be confirmed from the diffraction measurement result that the multi-lamellar structure as described above has a structure similar to that of the stratum corneum intercellular lipids, and an emulsion having the multi-lamellar emulsion structure prepared according to an exemplary embodiment of the present invention is suitable for a useful drug delivery system capable of simultaneously obtaining a dermatologically useful effect of the multi-lamellar emulsion itself in addition to efficacy of drugs applied to skin diseases or other transdermal delivery.

It is preferable that the drug is partitioned into the stratum corneum of the skin. Further, a content of the lipids and the emulsifier may be 5 to 30 wt %, a content of the drug for transdermal administration may be 0.001 to 25 wt %, and a sum of long-chain amides and sterols in the lipid ingredient may be 0.1 to 10 wt %, based on the entire composition.

As a preferable aspect of the present invention, the multi-lamellar emulsion structure may have a layered structure composed of a long periodicity phase (LPP) and a short periodicity phase (SPP) in a temperature range of 10° C. to 30° C. More preferably, the layered structure may be composed of a long periodicity phase of 10 to 30 nm and a short periodicity phase of 3 to 6 nm. Two or more long periodicity phases and short periodicity phases are structural features describing the lamellar structure, which is the most representative feature in view of molecular arrangement of the stratum corneum intercellular lipids of the skin, and a fact that two or more periodicity phases are shown in a multi-lamellar emulsion formulation indicates structural similarity between the multi-lamellar emulsion formulation and the stratum corneum intercellular lipids. The feature as described above indicates that the formulation according to the present invention may structurally allow the drug to be effectively partitioned in the stratum corneum intercellular space. Due to the structural feature as described above, which is similar to that of a lamellar structure of the skin stratum corneum, the multi-lamellar emulsion formulation may have an excellent skin barrier function, and have a significantly excellent effect on protecting the skin, and particularly, the multi-lamellar emulsion structure may be useful for stably delivering and preserving the drug. In the case in which the multi-lamellar emulsions structure does not have the periodicity phase, or the long periodicity phase or short periodicity phase is out of the above-mentioned range, a drug partitioning effect and dissolution rate of the active ingredient for transdermal administration may be deteriorated.

As another Preferable aspect of the preset invention, the multi-lamellar emulsion structure may have at least one liquid crystal mesophase at the time of analysis using differential scanning calorimeter (DSC), and an endothermic enthalpy in the liquid crystal mesophase may be 20 J/g or less.

The liquid crystal mesophase, which increases the dermatologically useful effect of the multi-lamellar emulsion structure itself, may be effective in view of improving a repair function of a skin barrier as well as drug delivery. The structure as described above may repair functions of the skin itself, allow a high concentration of a steroid not to penetrate into the skin in a short time, and allow a concentration of the steroid to be continuously and constantly maintained in the skin at the time of administering the topical steroid, which is significantly effective in inflammatory skin diseases as a local anti-inflammatory agent, thereby making it possible to decrease adverse effects while increasing treatment efficiency.

Further, as another preferable aspect, the multi-lamellar emulsion structure may have optical anisotropy of a maltese cross shape in cross-polarized microscope. Further, the formulation may be preferably an emulsion, a cream, a lotion, or a paste, but is not limited thereto.

The multi-lamellar emulsion (MLE) formulation may mean an emulsion prepared in a form in which an oily core is present at the center thereof, and a multilayered lamellar liquid crystalline structure encloses therearound. The present inventors found that due to a stabilized oil layer, the multilayered lamellar liquid crystalline structure of the MLE formulation may be usefully utilized for stably preserving an active ingredient which is weak against light or oxygen, and the multilayered lamellar liquid crystalline structure is useful as a drug delivery system for continuously delivering a drug, thereby completing the present invention.

In the present invention, the term "transdermal" means drug delivery through the skin or mucosal tissue. Therefore, unless specified in detail, the terms "transdermal" and "transmucosal" may be used compatibly with each other. Similarly, unless specified in detail, the terms "skin", "dermis", "epidermis", "mucous membrane", and similar terms may also be used compatibly with each other.

A representative example of the long-chain amide used in the present invention may include ceramides found in the skin, and any of natural ceramides, synthetic ceramides, or pseudo ceramides may be used. The natural ceramides, which are ceramides existing naturally, may include ceramide-1, ceramide-2, ceramide-3, ceramide-4, ceramide-5, ceramide-6, ceramide-7, ceramide-8, and the like, and the pseudo ceramides may include ceramide-104, ceramide-102, and the like. Plant-derived natural ceramides may include ceramide, cerebroside, monoglycosylceramide, oligoglycosylceramide, phytoceramide, and the like. An example of the synthetic ceramide may include ceramide-III ($C_{36}H_{73}NO_4$). The ceramide is known as a very important material for moisturizing and protecting the skin, and is synthesized so as to have the same structure as that in the human body or similarly deformed and synthesized to thereby be used. In the present invention, ceramide analogues such as myristoyl oxostearamide MEA, myristoyl oxoarachamide MEA, palmitoyl oxostearamide MEA, palmitoyl oxoarachamide MEA, commercialized PC-9S (Neopharm Co., Ltd., Korea) consisting of a mixture of these four compounds, dihydroxyisopropyl palmoylpalmamide, or a ceramide having the same structure as that of the synthetic ceramide such as ceramide-3 may be used. In addition, a suitable mixture thereof may also be used. Preferably, a content thereof may be 0.01 to 5 wt % based on the entire multi-lamellar emulsion.

The sterols used in the present invention may have a plate structure of a fused ring to contribute to stably maintaining the multi-lamellar emulsion. The sterol used in the present invention is at least one compound selected from the group consisting of cholesterol, cholesteryl sulfate, cholesteryl acetate, cholesteryl stearate, cholesteryl isostearate, cholesteryl hydroxystearate, and phytosterols, but is not limited thereto. One or a mixture of cholesterols and plant-derived phytosterols may be used. Preferably, a content thereof may be 0.01 to 10 wt % based on the entire multi-lamellar emulsion.

As the fatty acid used in the present invention, any one or more of fatty acids having 14 to 22 carbon atoms may be used. For example, in the present invention, palmitic acid, stearic acid, or ardchidic acid may be suitable, but the fatty acid is not limited thereto. Preferably, a content thereof may be 0.1 to 20 wt % based on the entire multi-lamellar emulsion.

As the fatty alcohol used in the present invention, any one or more of fatty alcohols having 14 to 22 carbon atoms may be used. For example, in the present invention, cetyl alcohol, stearyl alcohol, cetearyl alcohol, or behenyl alcohol may be suitable, but the fatty alcohol is not limited thereto. Each of the fatty acids and the fatty alcohols may be used alone, or a mixture thereof may be used. Preferably, a content thereof may be 0.1 to 20 wt % based on the entire multi-lamellar emulsion.

As the emulsifier used in the present invention, any emulsifier may be used without limitation as long as it is suitable for forming the multi-lamellar emulsion structure, For example, a polyglycerin based emulsifier such as polyglyceryl-10 dipalmitate, polyglyceryl-10 distearate, polyglyceryl-10 stearate, polyglyceryl-10 oleate, or the like; a sugar ester based emulsifier such as sorbitan palmitate, sorbitan stearate, sorbitan isostearate, sorbitan sesquistearate, sorbitan oleate, sorbitan sesquioleate, sorbitan olivate, sucrose cocoate, or the like; a glyceryl ester based emulsifier such as glyceryl stearate, glyceryl oleate, or the like; and a hydrogenated emulsifiers such as hydrogenated lecithin, hydrogenated palm glyceride, or the like, may be used. Preferably, a content thereof may be 1 to 15 wt % based on the entire multi-lamellar emulsion.

As the oil used in the present invention, any of saturated hydrocarbon based oils or unsaturated hydrocarbon based oils may be used, and a mixture thereof may also be used. In the present invention, any oil may be used without particular limitation. As the saturated hydrocarbon based oils, there are mineral oils and synthetic oils. An example thereof may include liquid paraffin, squalane, Vaseline, paraffin wax, other branched hydrocarbon based oils, or the like. As the unsaturated hydrocarbon based oils, there are general natural oils such as animal oils, vegetable oils, and the like. All of them may be used in the present invention. In the present invention, only one kind of oil may be used, but it is more preferably to use a mixture of various kinds of oils. The reason is as follows: in a case of preparing the multi-lamellar emulsion using only one kind of oil, generally, the saturated hydrocarbon based oil is not advantageous in forming the multi-lamellar emulsion but is advantageous in stabilizing a dermatologically useful lipophilic substance, and among the unsaturated hydrocarbon based oils, general natural oil in a triglyceride form is advantageous in forming the multi-lamellar emulsion but is disadvantageous in stabilizing the dermatologically useful lipophilic substance as compared to the saturated hydrocarbon based oil.

Therefore, the multi-lamellar emulsion is prepared using a mixture of various kinds of oils, which is advantageous in stabilizing the dermatologically useful lipophilic substance in addition to appropriate formation of the multi-lamellar emulsion. Further, at the time of preparing a multi-lamellar emulsion containing a steroid ingredient, it may be advantageous to use a mixture of various kinds of oils. Preferably, a content of the oil may be 1 to 30 wt % based on the entire multi-lamellar emulsion.

Preferably, a mixed amount of the lipid and the emulsifier, which are ingredients stably maintaining the emulsion may be 5 to 30 wt % based on the entire composition. In a case in which the content of the lipid and the emulsifier is low, it may be difficult to stabilize the emulsion through liquid crystal formation, and in a case in which the content is excessively high, the lipid and the emulsifier may restrict uses of other ingredients, such that it may be difficult to prepare formulations having various sensory feelings. Further, preferably, a sum of the long-chain amide and sterol among the lipid ingredients may be 0.1 to 10 wt %. In a case in which the content is low, the liquid crystal may be inappropriately formed, or stability may be deteriorated, and in a case in which the content is excessively high, stability may be deteriorated due to precipitation depending on a change in temperature. Further, as a result of various studies, it is preferable that a weight ratio of the long-chain amide and sterol ingredient is 0.1 to 10.

A pharmaceutically active ingredient or active substance (which may also be referred to as "drug") of the present invention may be a drug capable of having a local or systemic effect at the time of administration to the skin, and is not particularly limited. Several examples thereof may include anti-inflammatory drugs including both steroidal anti-inflammatory drugs (for example, hydrocortisone, prednisone, triamcinolone) and non-steroidal anti-inflammatory drugs (for example, naproxen, piroxicam); bacterial growth inhibitors (for example, chlorhexidine, hexylresorcinol); antimicrobial agents (for example, penicillins such as penicillin V, cephalosporins such as cephalexin, erythromycin, tetracycline, gentamicin, sulfathiazole, nitrofurantoine, quinolones such as norfloxacin, flumequine, levofloxacin); antiprotozoal agent (for example, metronidazole); antifungal agents (for example, nystatin); coronary vasodilators; calcium channel blockers (for example, nifedipine, diltiazem); bronchodilators (for example, theophylline, pirbuterol, salmeterol, isoproterenol); enzyme inhibitors such as collagenase inhibitors, protease inhibitors, elastase inhibitors, lipoxygenase inhibitors (for example, A64077), and angiotensin converting enzyme inhibitors (for example, captopril, lisinopril); other antihypertensive agents (for example, propranolol); leukotriene antagonists (for example, ICI204, 219); anti-ulcer agents such as H2 antagonists; steroidal hormones (for example, progesterone, testosterone, estradiol); antiviral drugs and/or immunomodulators (for example, 1-isobutyl-1H-imidazo[4,5-c]quinoline-4-amine, 1-(2-hydroxy-2-methylpropyl)-1H-imidazo[4,5-c]quinoline-4-amine, and acyclovir); local anesthetics (for example, benzocaine, propofol); cardiac stimulants (for example, digitalis, digoxin); cough medicines (for example, codeine, dextromethorphan); antihistamines (for example, diphenhydramine, chlorpheniramine, terfenadine); narcotic analgesics (for example, morphine, buprenorphine); peptide hormones (for example, human or animal growth hormones, luteinizing hormone releasing hormone (LHRH); cardioactive agents such as atriopeptin; proteinaceous products (for example, insulin); enzymes (for example, anti-plaque enzymes, lysozyme, dextranase); motion sickness remedies; anticonvulsants (for example, carbamazine); immunosuppressants (for example, cyclosporine); mental drugs (for example, diazepam); depressants (for example, phenobarbital); anticoagulants (for example, heparin); analgesics (for example, acetaminophen); migraine drugs (for example, ergotamine, melatonin, sumatriptan); arrhythmia drugs (for example, flecainide); antiemetics (for example, metoclopramide, ondansetron); anticancer agents (for example, methotrexate); agents for neurological disorders, such as anti-anxiety drugs; hemostatics, anti-obesity drugs, and the like, and pharmaceutically acceptable salts and esters thereof. An amount of the drug constituting a pharmaceutically effective dose may be easily determined by those skilled in the art in consideration of a specific drug, a specific carrier, and the desired treatment effect. In the emulsion having the multi-lamellar structure according to the present invention, a content of the drug may be in a range of about 0.001 wt % to about 25 wt %, preferably, about 0.001 wt % to about 20 wt %, and most preferably about 0.01 wt % to about 10 wt %.

Preferably, the active ingredient in the present invention may be a steroid, and a usable example of the steroid includes progesterone, e.g., allylestrenol, anagestone, chlomardinone acetate, delmadinone acetate, demegestone, desogestrel, 3-keto desogestrel, dimethisterone, drospirenone, dydrogesterone, ethisterone, ethynodiol, flurogestone acetate, gestodene, gestonorone caproate, 17-hydroxy-16-methylene-delta-progesterone, 17-alpha-hydroxyprogesterone, hydroxyprogesterone, hydroxyprogesterone acetate, hydroxyprogesterone caproate, levonorgestrel, lynestrenol, medrogestone, medroxyprogesterone, medroxyprogesterone acetate, megestrol acetate, melengestrol, norethindrone, norethindrone acetate, norethynodrel, norgesterone, norgestimate, norgestrel, norgestrienone, norethisterone, norethynodrel, norvinisterone, pentagestrone, progesterone, promegestone, and trengestone.

Another example of the steroid includes non-steroidal estrogens such as benzestrol, broparoestrol, chlorotrianisene, dienestrol, diethylstilboestrol, diethylstilboestrol dipropionate, dimestrol, fosfestrol, hexoestrol, methallenestril, methestrol, and the like; and steroidal estrogens such as colpormon, conjugated estrogenic hormone, equilenin, equilin, estradiol and esters thereof (for example, estradiol benzoate, estradiol valerate, estradiol cypionate, estradiol decanoate, and estradiol acetate), estriol, estrone, ethinyl estradiol, mestranol, moxestrol, mytatrienediol, quinestradiol, quinestrol, and the like. Another example of the steroid includes corticosteroids such as betamethasone, betamethasone acetate, cortisone, hydrocortisone, hydrocortisone acetate, corticosterone, fluocinolone acetonide, prednisolone, prednisone, and triamcinolone; and androgens and anabolic agents such as aldosterone, androsterone, testosterone, and methyl testosterone.

As another example, there are androgens such as boldenone, cloxotestosterone, fluoxymesterone, mestanolone, mesteronolone, 17-methyl testosterone, 17-alpha-methyl testosterone 3-cyclopentyl enol ether, norethandrolone, normethandrone, oxandrolone, oxymesterone, oxymetholone, prasterone, stanolone, stanolozol, testosterone, tiomesterone; and glucocorticoids such as 21-acetoxypregnenolone, alclometasone, algestone, amcinonide, beclomethasone, bethamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, flucinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone-25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and the like. As additional steroids, there are noregestrel, levonoregestrel, norelgestromin, and derivatives thereof.

The steroid, which is a local anti-inflammatory agent, may significantly effectively act on inflammatory skin diseases (dermatitis, eczema), have an excellent effect with a small amount, be relatively easily used, and does not cause pain or odor, such that the steroid has been widely used in the inflammatory skin diseases. However, in a situation that damage of the skin barrier function acts as a primary factor or aggravating factor in most of the skin diseases, the steroid may not basically treat the skin diseases. On the contrary, in a case of using the steroid for a long period of time, the steroid may decrease formation of stratum corneum intercellular lipids of the skin, imparting the skin barrier function, the skin barrier function is rather deteriorated, and synthesis of collagen and elastin may also be decreased, thereby causing adverse effects such as acne, hypertrichosis, striae distensae, folliculitis, contact dermatitis, secondary infection, or the like. Therefore, the present inventors tried to develop a formulation capable of increasing treatment efficiency and decreasing adverse effects by allowing a high concentration of the steroid not to infiltrate in the skin in a short time and allowing a suitable concentration of the steroid to be continuously maintained and absorbed in the skin while repairing the skin barrier function, and the present inventors confirmed that the drug delivery system having a multi-lamellar structure may repair the skin barrier function, significantly improve symptoms of the diseases, and have small adverse effects.

Further, another preferable drug in the present invention may be non-steroidal anti-inflammatory drug (NSAID). As the NSAID, one or more selected from phenylpropionic acid derivative based NSAIDs including ketoprofen, flurbiprofen, fenoprofen, and ibuprofen; oxicam derivative based NSAIDs including piroxicam, tenoxicam, and meloxicam; diclofenac; and indomethacin may be used. The NSAID has excellent drug efficacy and a long half time, such that the NSAID may be suitable for the drug for transdermal administration. Particularly, the formulation of the present invention may be significantly effective for promoting the partitioning of the drug in the stratum corneum of the skin to maintain constant drug efficacy.

Further, another preferable drug in the present invention may be one or more antifungal agents selected from amorolfine, isoconazole, clotrimazole, econazole, miconazole, nystatin, terbinafine, bifonazole, amphotericin, griseofulvin, ketoconazole, fluconazole, flucytosine, salicylic acid, fezatione, ticlatone, tolnaftate, triacetin, zinc pyrithione, and sodium pyrithione.

The transdermal drug delivery system may further contain other additives or excipient in addition to the pharmaceutically active ingredient. The additive may include a pharmaceutically acceptable material capable of being used as a dermal penetration enhancer (that is, a material increasing a penetration rate of a drug passing through or penetrating into the skin) or a solubilizer (that is, a material effectively solubilizing the drug) in the transdermal drug delivery system. In view of effectively penetrating the active ingredient into the skin, it is preferable that a material suitable for being used as the dermal penetration enhancer is one or more selected from the group consisting of fatty acids such as linoleic acid, oleic acid, palmitic acid, stearic acid, capric acid, and myristic acid; polyhydric alcohols such as propylene glycol, polyethylene glycol, dipropylene glycol, diethylene glycol, and glycerol; surfactants such as Tween 80, labrasol, and cremophor; fatty acid alcohols such as oleyl alcohol and stearyl alcohol; fatty acid esters such as isopropyl myristate, propylene glycol caprylate, propylene glycol laurate, and polyethylene glycol laurate; and non-ionic surfactants such as polyoxyethylene behenyl ether, polyoxyethylene hexyl decyl ether, and polyoxyethylene decyl tetradecyl ether. Example of other additives may include a tackifier, a plasiticizer, and an anti-oxidant.

In another general aspect, a pharmaceutical composition for external application contains an emulsion having the multi-lamellar emulsion structure as described above. A formulation of the pharmaceutical composition is not limited. As an example, plasters, lotions, liniments, liquids and solutions, aerosols, extracts, ointments, fluidextracts, emulsions, suspensions, capsules, creams, soft or hard gelatin capsules, patches, or sustained formulations, may be used. Meanwhile, the pharmaceutical composition may contain a pharmaceutically acceptable matrix; carriers; excipients; binders including starch, tragacanth gum, gelatin, molasses, polyvinyl alcohol, polyvinyl ether, polyvinyl pyrrolidone, hydroxypropyl cellulose, methyl cellulose, ethyl cellulose, and carboxymethyl cellulose; disintegrants including agar, starch, gelatin powder, carboxymethyl cellulose sodium, carboxymethylcellulose calcium, crystalline cellulose, calcium carbonate, sodium bicarbonate, and sodium alginate; lubricants including magnesium stearate, talc, hydrogenated vegetable oil; colorants, and the like. Examples of the carrier and the excipient may include lactose, glucose, sucrose, mannitol, potato starch, corn starch, calcium carbonate, calcium phosphate, cellulose, and the like. Adjuvants such as stabilizers, solubilizing agents, transdermal absorption accelerators, or the like, or additives such as aromatics, preservatives, or the like, may be further added in addition to the above-mentioned additives.

Meanwhile, a standard dose of the composition for external application on the skin according to the present invention for various patients may be changed depending on individual characteristics of the patients, and a substantially skilled clinician may determine an ideal dose for the composition for external application on the skin according to the present invention and an administration plan, for example, the most suitable treatment strategies in view of specific requirements and overall conditions of the patients. At the time of determining a suitable dose of the composition for external application on the skin according to the present invention, various reference documents may be referred to. Further, the suitable dose of the composition for external application on the skin according to the present invention may be generally determined from in vitro or animal model studies. For example, a suitable dose may be determined by adding of composition for external application on the skin according to the present invention to target cells at various concentrations in vitro.

In the transdermal drug delivery system having a multi-lamellar emulsion structure, the long periodicity phase (LPP) and the short periodicity phase (SPP) are shown as shown in the stratum corneum of the skin, such that a similarity to the lamellar structure of the stratum corneum of the skin is significantly high. Therefore, in a case of using the transdermal drug delivery system as at least one drug delivery system for transdermal absorption, the transdermal delivery system may allow the drug to be effectively partitioned into the skin, particularly, the stratum corneum, may have an effect of rapidly repairing the skin barrier in the damaged skin, and may be significantly useful for recovering functions of the skin, whereby the transdermal drug delivery system may become an effective drug delivery system for transdermal delivery.

Advantageous Effects

Since a transdermal drug delivery system having a multi-lamellar emulsion structure according to the present invention has high compatibility with stratum corneum intercellular lipids due to a lamellar structure in which a layered structure visible in the stratum corneum intercellular lipids of the human body is repeated, the transdermal drug delivery system having a multi-lamellar emulsion structure may promote partitioning of an active ingredient from a matrix into the stratum corneum intercellular lipids. Therefore, the transdermal drug delivery system having a multi-lamellar emulsion structure may increase a content of the drug in the stratum corneum and improve a drug storage function of the stratum corneum to enable continuous administration of the drug, thereby making it possible to achieve an excellent drug delivery effect.

BEST MODE

Hereinafter, the present invention will be described in more detail through Examples. However, these Examples are only to illustrate the present invention, and a scope of the present invention is not limited to these Examples.

Examples 1 and 2

Preparation of Formulation for Transdermal Drug Delivery According to Present Invention A liquid crystal emulsion was prepared by mixing a long-chain amide, sterol, fatty acid, fatty alcohol, and non-ionic surfactant, a thickener, and purified water depending on the composition ingredients and composition ratio illustrated in the following Table 1. As an active ingredient, steroidal and non-steroidal anti-inflammatory drugs were each used. As the long-chain amide, myristoyl/palmitoyl oxostearamide/arachamide MEA (Neopharm, product name: PC-9S) was used.

TABLE 1

| Raw Material | Example 1 | Example 2 |
| --- | --- | --- |
| Pseudo-ceramide (PC-9S) | 0.60 | 0.60 |
| Cholesterol | 0.20 | 0.20 |
| Stearic acid | 1.50 | 1.50 |
| Cetanol | 5.00 | 5.00 |
| Glycerin monostearate | 1.50 | 1.50 |
| Polyoxyethylene glyceryl monostearate 15 | 2.50 | 0.50 |
| Polyoxyethylene glyceryl monostearate 10 | 1.00 | 1.00 |
| Polysorbate 60 | | |
| Squalane | 1.00 | 1.00 |
| Olive oil | 2.00 | 2.00 |
| Light liquid paraffin | | |
| 1,3-Butylene Glycol | 10.00 | 10.00 |
| Isopropyl myristate | | |
| Concentrated Glycerin | | |
| Butylhydroxytoluene | 0.02 | 0.02 |
| Propyl paraben | 0.05 | 0.05 |
| Methyl paraben | 0.10 | 0.10 |
| Benzyl alcohol | | |
| Chloro-cresol | | |
| Carbomer | | |
| Sodium hydroxide | | |
| Trolamine | | |
| Sodium hydrogen phosphate hydrate | | |
| Purified water | q.s. | q.s. |
| Hydrocortisone | 1.00 | |
| Ketoprofen | | 3.00 |

Comparative Examples 1 and 2

For comparison with the Examples, in Comparative Examples, an existing drug containing the same active ingredient available on the market was purchased and used. In the Comparative Examples, product names, manufacturers, and lot numbers were illustrated in the following Table 2, respectively.

TABLE 2

| Comparative Example 1 | Comparative Example 2 |
| --- | --- |
| Cortaid cream | Ketopain Gel |
| (1% Hydrocortisone) | (3% ketoprofen) |
| (Johnson & Johnson) | (TAI GUK Pharm.) |
| (Lot No.: 20316TM7) | (Lot No.: 15008) |

Example 3

Small Angle X-Ray Diffraction (SXRD) Analysis

Figure 3:
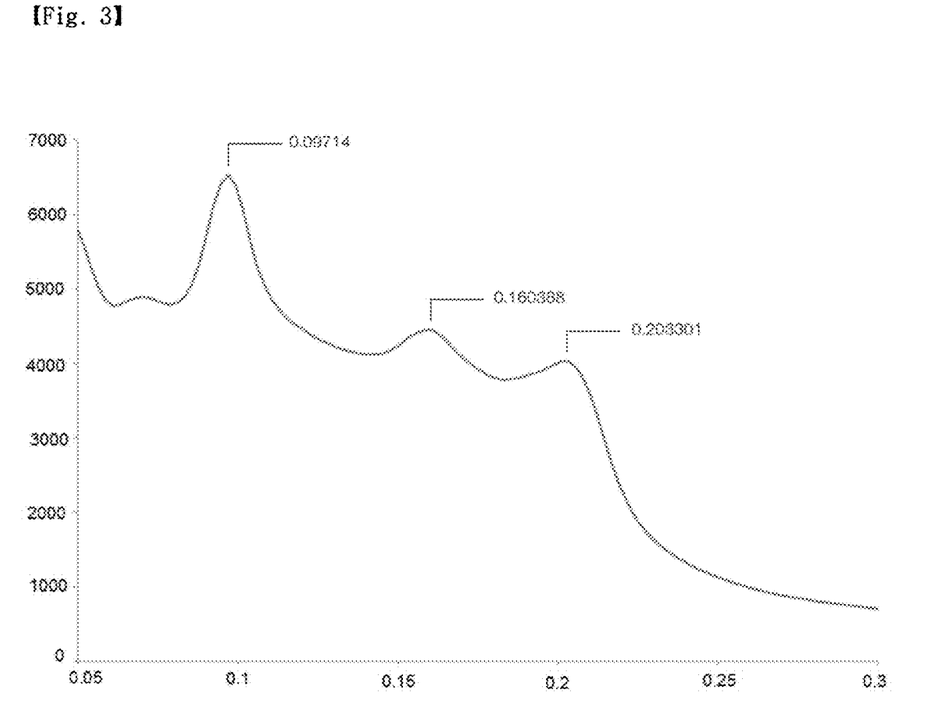
FIG. 3 illustrates results obtained by analyzing a multi-lamellar emulsion according to the present invention using small angle X-ray diffraction (SXRD).

In order to analyze the multi-lamellar structure of the formulation in Example 1, small angle X-ray diffraction analysis was performed while increasing a temperature, thereby obtaining analysis results. The small angle X-ray diffraction analysis was performed using a method disclosed in the reference document (Journal of Controlled Release vol. 115, pp 275-279, 2006). X-ray diffraction was measured using monochromatic synchrotron equipment at BL15A Station in Photo Factory (Ibaraki, Japan). A wavelength of the X-ray was 0.1506 nm, and a distance between a sample and a detector was about 150 nm. X-ray diffraction was recorded using an imaging plate (Type BAS-III, FujiFilm, Japan), and a diffraction intensity was measured using BAS2500 system (FujiFilm, Japan). The results were illustrated in FIG. 3, in the multi-lamellar structure, a long periodicity phase (LPP) and a short periodicity phase (SPP) were regularly observed, and at an initial measuring temperature of 20° C., peaks (0.09714 and 0.203301) having a long periodicity phase of about 10.2 nm and a peak (0.16388) having a short periodicity phase of 6.2 nm were detected. It may be confirmed from the diffraction measurement results that the multi-lamellar structure had a structure similar to the structure of the stratum corneum intercellular lipids.

Example 4

Differential Scanning Calorimeter (DSC) Analysis

Figure 4:
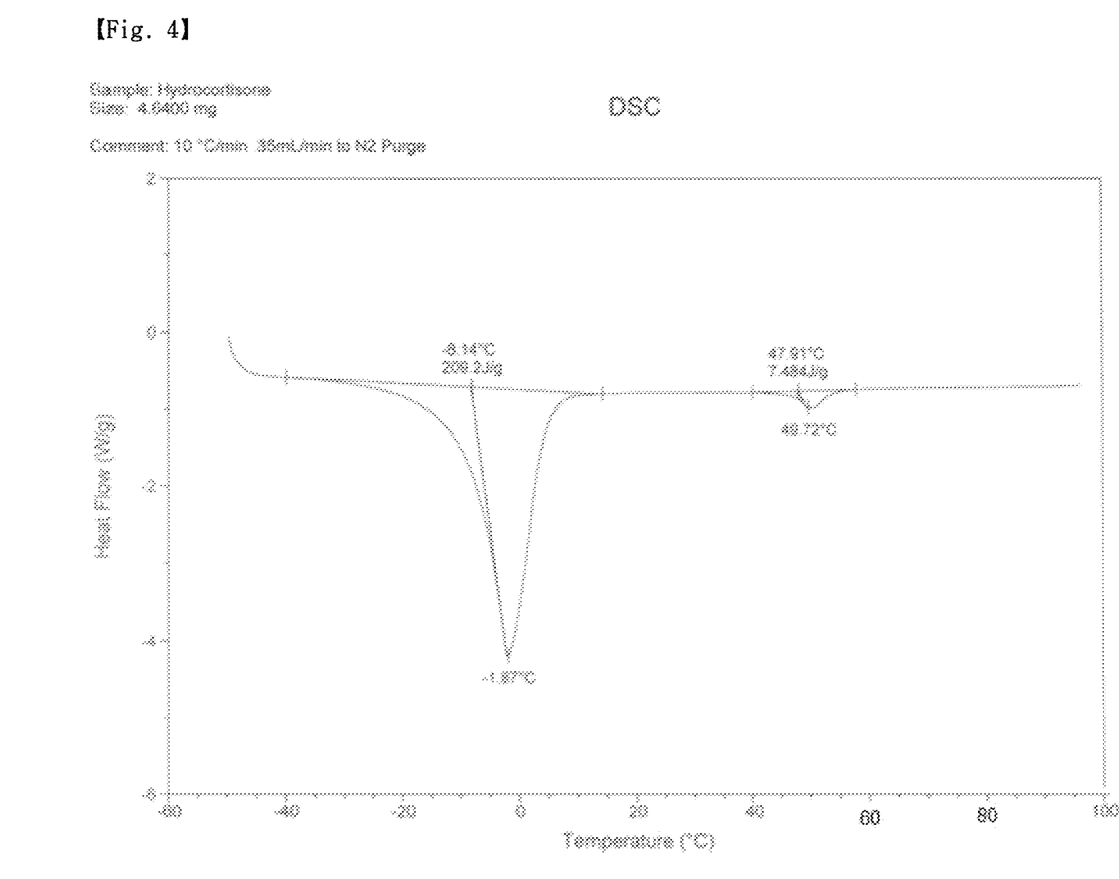
FIG. 4 illustrates results obtained by analyzing the multi-lamellar emulsion according to the present invention using differential scanning calorimeter (DSC).

In order to observe phase transition depending on a change in temperature, the formulation of Example 1 was analyzed using differential scanning calorimeter (DSC Q1000 V9.9 Build 303). As a result, one liquid crystal mesophase was shown under a heating condition as illustrated in FIG. 4, and endothermic enthalpy was 7.484 J/g.

Example 5

Cross-Polarized Microscope Analysis

Figure 5:
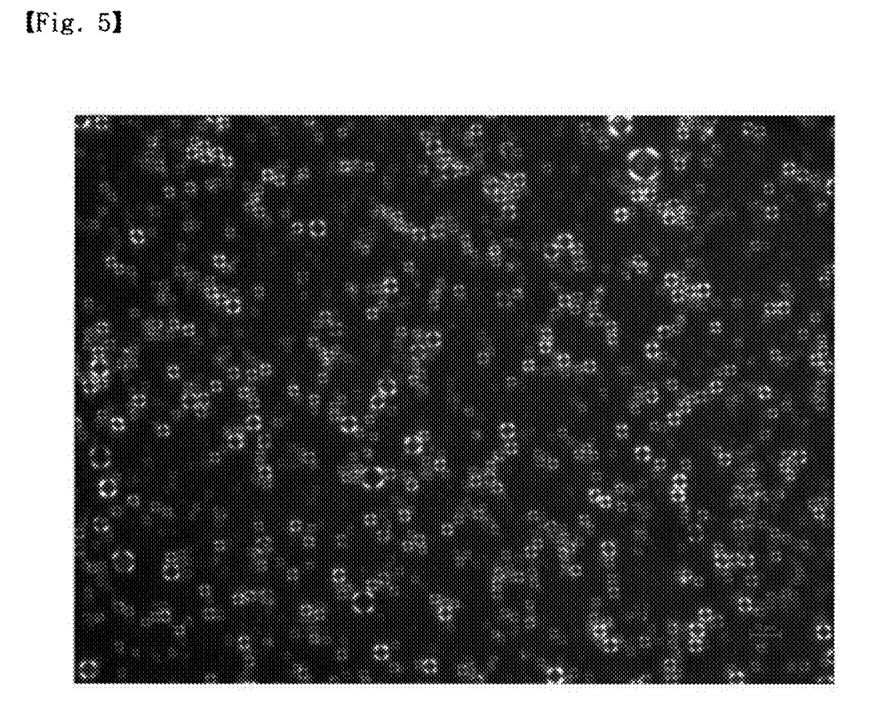
FIG. 5 illustrates results obtained by analyzing the multi-lamellar emulsion according to the present invention using a cross-polarized microscope.

In order to analyze optical properties of the formulation of Example 1, the formulation was observed using a cross-polarized microscope (Optiphot-2, Nikon). The result was illustrated in FIG. 5, and it may be confirmed that the formulation had optical anisotropy of a maltese cross shape.

Experimental Example 1

Transdermal Permeability Measurement

Transdermal permeabilities of the hydrocortisone materials in the formulations of Example 1 (K17838 Atopalm) and Comparative Example 1 (K17836 Cortaid) were compared with each other.

After storing the human skin obtained by resection performed for cosmetic purposes at 4° C. immediately after extraction, a subcutaneous fat layer was removed. After marking a classification number, each of the skin sections was stored at −20° C., and used in experiments later. After the stored skin section was melted at room temperature, the dermis was cut using a dermatome so that the skin had a thickness of about 500 μm. Punch biopsy (diameter: 24 mm) was performed on the cut skin, tissue to be used in an experiment was secured, and each of the tissue was fixed on Franz Cells, such that a permeability test proceeded. A drug was applied over an area of about 1.77 $cm^2$, and a receptor chamber was filled with KRB buffer/Nonidet, such that the experiment proceeded. At the time of the experiment, a temperature was maintained at 32° C., and after 300 μl of solution was each extracted from the receptor chamber after 3 hours, 5 hours, 6 hours, 21 hours, 22 hours, and 23 hours, an amount of hydrocortisone permeated through the skin was analyzed using high-performance liquid chromatography (HPLC)/mass spectrometry (MS) equipment.

Figure 1:
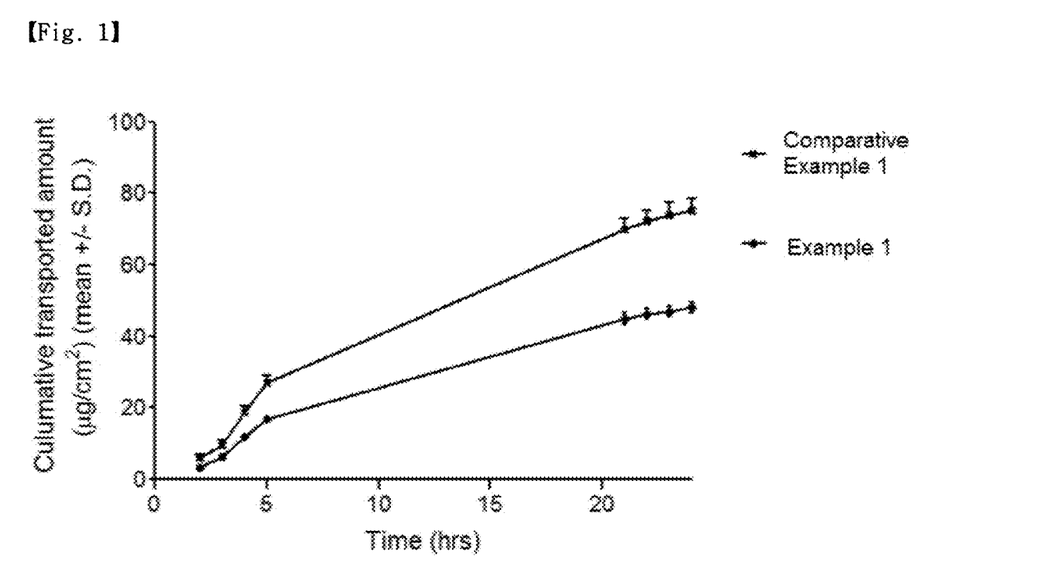
FIG. 1 is a graph illustrating transdermal permeability of hydrocortisone, an active ingredient.

The results were illustrated in transdermal permeability measurement results of FIG. 1. As illustrated in the graph, it was observed that transdermal permeability of the formulation of Example 1 according to the present invention was lower than that in Comparative Example 1 (Cortaid).

Experimental Example 2

Drug Content Measurement in Stratum Corneum and Skin

With respect to the hydrocortisone materials in the formulations of Example 1 (K17838 Atopalm) and Comparative Example 1 (K17836 Cortaid), after a predetermined time from application on the skin, concentrations of the drug in the stratum corneum, the epidermis, and the dermis were compared with each other.

After storing the human skin obtained by resection performed for cosmetic purposes at 4° C. immediately after extraction, a subcutaneous fat layer was removed. After marking a classification number, each of the skin sections was stored at −20° C., and used in experiments later. After the stored skin section was melted at room temperature, the dermis was cut using a dermatome equipment so that the skin had a thickness of about 500 μm. Punch biopsy (diameter: 24 mm) was performed on the cut skin, tissue to be used in an experiment was secured, and each of the tissue was fixed on a Saarburker model. After applying the sample, a temperature was maintained at 32° C., and a product on the skin surface was removed after 6 hours. In order to separate the stratum corneum, the epidermis, and the dermis, a tape stripping method and a cryosection method were used. The stratum corneum of the skin was separated by repeating a process of attaching a tape so as to expose an area of 2.01 cm$^2$ and detaching the tape 20 times. After the initial 2 tapes were separately stored, contents of hydrocortisone in 18 tapes were measured. The tissue from which the stratum corneum was removed was subjected to cryosection again, such that each of the layers was separated. Contents of hydrocortisone in the tissue were measured by dividing the tissue into a total of four fractions.

Figure 2:
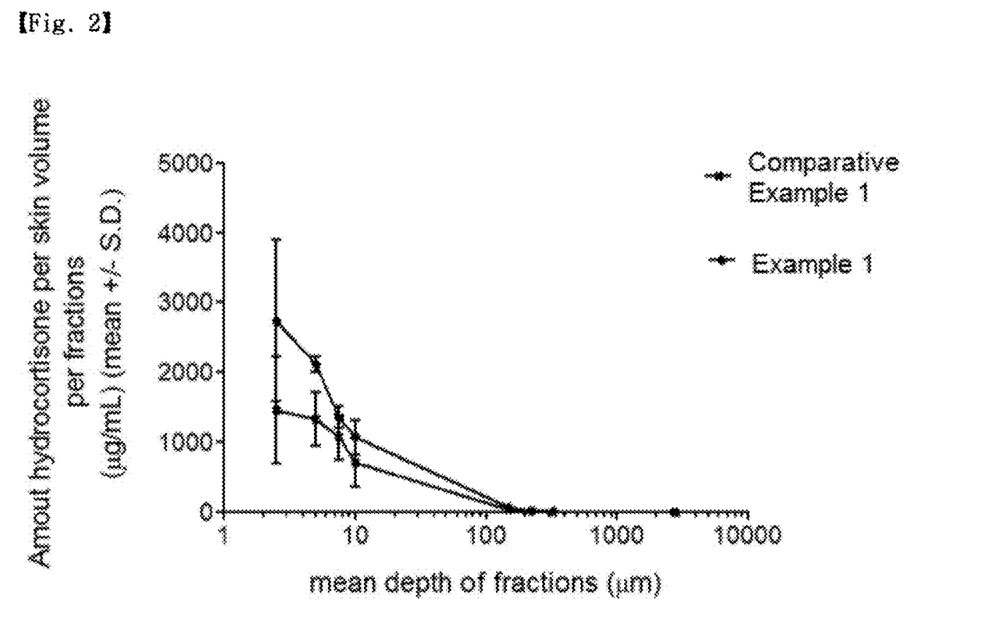
FIG. 2 is a graph illustrating a result obtained by measuring a deposition amount of hydrocortisone, the active ingredient, on the skin.

The results were illustrated in drug content measurement results in the stratum corneum of the skin of FIG. 2. As illustrated in the graph, in the case of the formulation of Example 1 according to the present invention, the concentration of the drug in the stratum corneum was at most about 1.6 times higher than that in Comparative Example 1 (Cortaid), and thus it was proven that the formulation of Example 1 had an excellent partitioning effect in the stratum corneum.

Experimental Example 3

Drug Release Rate Measurement

In order to measure drug release from formulations with respect to the formulations including individual drugs prepared in the Example and Comparative Examples, drug release rates were measured using a Durapore membrane (Millipore). After installing the Durapore membrane onto Franz cells, each of the drugs was applied, and drug release was measured for 6 hours, thereby confirming the results illustrated in FIG. 3.

TABLE 3

| Example or Comparative Example Sample | Content (ppm) | Dissolution test 6 h (ppm) | Ratio (%) (API Permeation/ API Total) |
| --- | --- | --- | --- |
| Example 1 | 10000 | 54.11037 | 0.54110 |
| Comparative Example 1 | 10000 | 130.77252 | 1.30773 |
| Example 2 | 30000 | 144.86849 | 0.48289 |
| Comparative Example 2 | 30000 | 674.82782 | 2.24943 |

As a measurement result, it was observed that high drug release was exhibited in the Comparative Examples, as compared to the Example.

Experimental Example 4

Drug Permeation Measurement Through Artificial Membrane

With respect to the formulations including individual drugs prepared in the Example and Comparative Examples, drug permeation through a Strat-M membrane (Millipore) corresponding to a membrane having a structure similar to that of the Stratum Corneum of the skin in the human body was measured. The Strat-M membrane was known as a membrane having a permeation behavior similar to that of the stratum corneum of the human body by coating a lipid membrane made of ingredients similar to those of the stratum corneum of the human body on a synthesized filtration membrane. After 24 hours of installing the Strat-M membrane onto the Franz cell and applying a predetermined amount of each of the drugs, permeation amounts of the drugs were measured, thereby obtaining results as illustrated in Table 4.

TABLE 4

| Examples and Comparative Examples | Content (ppm) | Permeation test 24 h (ppm) | Ratio (%) (API Permeation/ API Total) |
| --- | --- | --- | --- |
| Example 1 | 10000 | 32.96378 | 0.32964 |
| Comparative Example 1 | 10000 | 3.47714 | 0.03477 |
| Example 2 | 30000 | 267.81670 | 0.89272 |
| Comparative Example 2 | 30000 | 168.67610 | 0.56225 |

In contrast with the drug release illustrated in Table 3, it was observed that high drug permeation through the Strat-M was rather exhibited in the Example.

Experimental Example 5

Drug Permeability Through Skin in Animal Test

After applying 1 g of drugs on the skin of a mouse and a micropig as illustrated in the following Table 5 using the formulations of Example 1 and Comparative Example 1, respectively, permeability after 24 hours was measured.

TABLE 5

| Animal | Examples Comparative Examples | Content (ppm) | Permeation 24 h (ppm) | Ratio (%) (API Permeation/ API Total*100) |
| --- | --- | --- | --- | --- |
| Mouse | Example 1 | 10000 | 1.10967 | 0.01110 |
| | Comparative Example 1 | 10000 | 3.08297 | 0.03083 |
| Micropig | Example 1 | 10000 | 0.22005 | 0.00220 |
| | Comparative Example 1 | 10000 | 0.94203 | 0.00942 |

Similarly to the experimental results using the skin of the human body, skin permeation in the Comparative Example was about 3 to 4 times higher than in the Example.

Experimental Example 6

Drug Deposition Amount in Skin in Animal Test

After applying 1 g of drugs on the skin of a mouse and a micropig as illustrated in the following Table 6 using the formulations of Example 1 and Comparative Example 1, respectively, contents of the drugs in the skin after 24 hours were measured.

TABLE 6

| Animal | Examples and Comparative Examples | Content (ppm) | permeation 24 h (ppm) | Ratio (%) (API Permeation/ API Total*100) |
|---|---|---|---|---|
| Mouse | Example 1 | 10000 | 32.85673 | 0.32857 |
| | Comparative Example 1 | 10000 | 55.81827 | 0.55818 |
| Micropig | Example 1 | 10000 | 137.33199 | 1.37332 |
| | Comparative Example 1 | 10000 | 123.11263 | 1.23113 |

As illustrated in the experimental results, in the experiment using the micropig, the content of the drug in the skin was higher than that in Comparative Example.

As in the experimental result, as a result of the small angle X-ray diffraction analysis of the transdermal drug delivery system including the emulsion used in the Example of the present invention, peaks (0.09714 and 0.203301) having a long periodicity phase of about 10.2 nm and a peak (0.16388) having a short periodicity phase of 6.2 nm were detected. It may be confirmed from the diffraction measurement result that the multi-lamellar structure as described above has a structure similar to that of the stratum corneum intercellular lipids, and is suitable for a useful drug delivery system capable of simultaneously obtaining a dermatologically useful effect of the multi-lamellar emulsion itself in addition to efficacy of drugs applied to skin diseases or other transdermal delivery.

The invention claimed is:

1. A transdermal drug delivery system, which is a delivery system for transdermal absorption, having a multi-lamellar emulsion structure, comprising:
    lipids including a long-chain amide, a sterol, a fatty acid and a fatty alcohol;
    an emulsifier;
    an oil; and
    at least one active ingredient for transdermal administration,
    wherein a content of the lipids and the emulsifier is 5 to 30 wt %, a content of the active ingredient for transdermal administration is 0.001 to 25 wt %, and a sum of the long-chain amide and the sterol in the lipids is 0.1 to 10 wt %, based on the entire composition,
    wherein the multi-lamellar emulsion structure has a layered structure composed of a long periodicity phase and a short periodicity phase in a temperature range of 10° C. to 30° C., and
    wherein the long periodicity phase is 10 to 30 nm and the short periodicity phase is 3 to 6 nm.

2. The transdermal drug delivery system of claim 1, wherein the multi-lamellar emulsion structure simultaneously has a periodicity phase of 9.0 to 11.0 nm and a periodicity phase of 5.2 to 7.2 nm in small angle X-ray diffraction analysis.

3. The transdermal drug delivery system of claim 1, wherein the active ingredient is partitioned in the stratum corneum of the skin.

4. The transdermal drug delivery system of claim 1, wherein at the time of analysis using differential scanning calorimeter, the multi-lamellar emulsion structure has at least one liquid crystal mesophase and an endothermic enthalpy is 20 J/g or less.

5. The transdermal drug delivery system of claim 1, wherein the multi-lamellar emulsion structure has optical anisotropy of a maltese cross shape in cross-polarized microscope.

6. The transdermal drug delivery system of claim 1, wherein a formulation of the drug delivery system is an emulsion, a cream, a lotion, or a paste.

7. The transdermal drug delivery system of claim 1, wherein the long-chain amide is at least one compound selected from the group consisting of myristoyl oxostearamide MEA, myristoyl oxoarachamide MEA, palmitoyl oxostearamide MEA, palmitoyl oxoarachamide MEA, dihydroxyisopropyl palmoylpalmamide, ceramide-1, ceramide-2, ceramide-3, ceramide-3B, ceramide-4, ceramide-5, and ceramide-6.

8. The transdermal drug delivery system of claim 1, wherein the sterol is at least one compound selected from the group consisting of cholesterol, cholesteryl sulfate, cholesteryl acetate, cholesteryl stearate, cholesteryl isostearate, cholesteryl hydroxystearate, and phytosterol.

9. The transdermal drug delivery system of claim 1, wherein the emulsifier is at least one compound selected from the group consisting of polyglycerin based emulsifiers; sugar ester based emulsifiers; glyceryl ester based emulsifiers; and hydrogenated emulsifiers.

10. The transdermal drug delivery system of claim 1, wherein the active ingredient is at least one of hydrocortisone based steroidal drugs, cortisone based steroidal drugs, and corticosterone based steroidal drugs.

11. The transdermal drug delivery system of claim 1, wherein the active ingredient is at least one non-steroidal anti-inflammatory drug (NSAID) selected from a phenylpropionic acid derivative based NSAID; an oxicam derivative based NSAID; diclofenac; and indomethacin.

12. A pharmaceutical composition for external application, comprising an emulsion having the multi-lamellar emulsion structure of claim 1.

13. The transdermal drug delivery system of claim 11, wherein the phenylpropionic acid derivative based NSAID includes ketoprofen, flurbiprofen, fenoprofen, and ibuprofen.

14. The transdermal drug delivery system of claim 11, wherein the oxicam derivative based NSAID includes piroxicam, tenoxicam, and meloxicam.

* * * * *